United States Patent
Hicks et al.

(10) Patent No.: US 7,275,423 B2
(45) Date of Patent: Oct. 2, 2007

(54) AUTOMATIC SPEED CALCULATION FOR SCRATCH MACHINE

(75) Inventors: David L. Hicks, Fowlerville, MI (US); Michael J. Niel, Redford, MI (US)

(73) Assignee: Toyota Technical Center USA, Inc., Ann Arbor, MI (US)

( * ) Notice: Subject to any disclaimer, the term of this patent is extended or adjusted under 35 U.S.C. 154(b) by 25 days.

(21) Appl. No.: 11/055,274

(22) Filed: Feb. 10, 2005

(65) Prior Publication Data

US 2006/0174699 A1    Aug. 10, 2006

(51) Int. Cl.
*G01N 3/46* (2006.01)
*G01N 33/00* (2006.01)
(52) U.S. Cl. ............................. 73/78; 73/104
(58) Field of Classification Search ............. 73/78, 73/104
See application file for complete search history.

(56) References Cited

U.S. PATENT DOCUMENTS

| | | | | |
|---|---|---|---|---|
| 3,676,777 A | * | 7/1972 | Charters | 324/754 |
| 4,791,807 A | | 12/1988 | Oechsle | 73/78 |
| 4,843,895 A | * | 7/1989 | Harper et al. | 73/865.9 |
| 5,359,879 A | | 11/1994 | Oliver et al. | 73/7 |
| 6,520,004 B1 | | 2/2003 | Lin | 73/81 |
| 6,631,647 B2 | | 10/2003 | Seale | 73/789 |

* cited by examiner

*Primary Examiner*—Thomas P. Noland
(74) *Attorney, Agent, or Firm*—Gifford, Krass, Sprinkle, Anderson & Citkowski, P.C.

(57) ABSTRACT

An improved surface testing apparatus, such as a scratch test apparatus, allows accurate determination of the test speed, for example using one or more magnetic sensors. An example scratch test apparatus comprises an arm assembly, and an attached blade moving over the surface during the scratch test. A pair of spaced apart reed switches are provided proximate to the arm assembly, the reed switches being successively actuated by a magnetic portion of the arm asssembly as it moves during the scratch test.

14 Claims, 3 Drawing Sheets

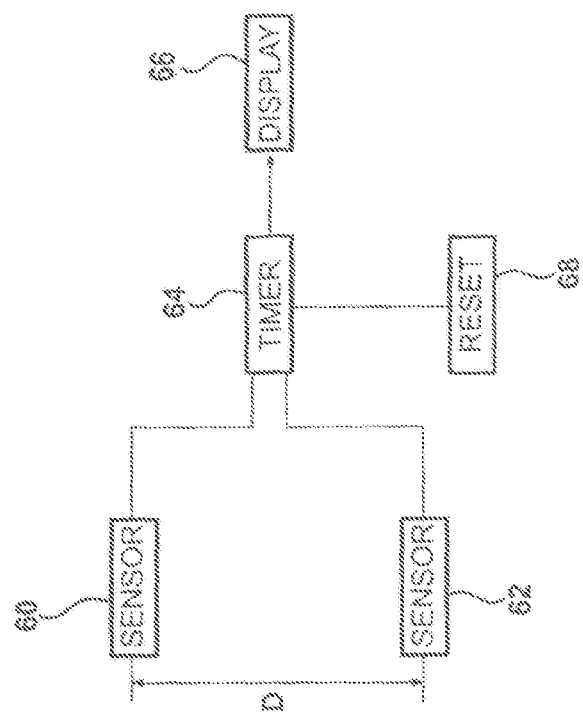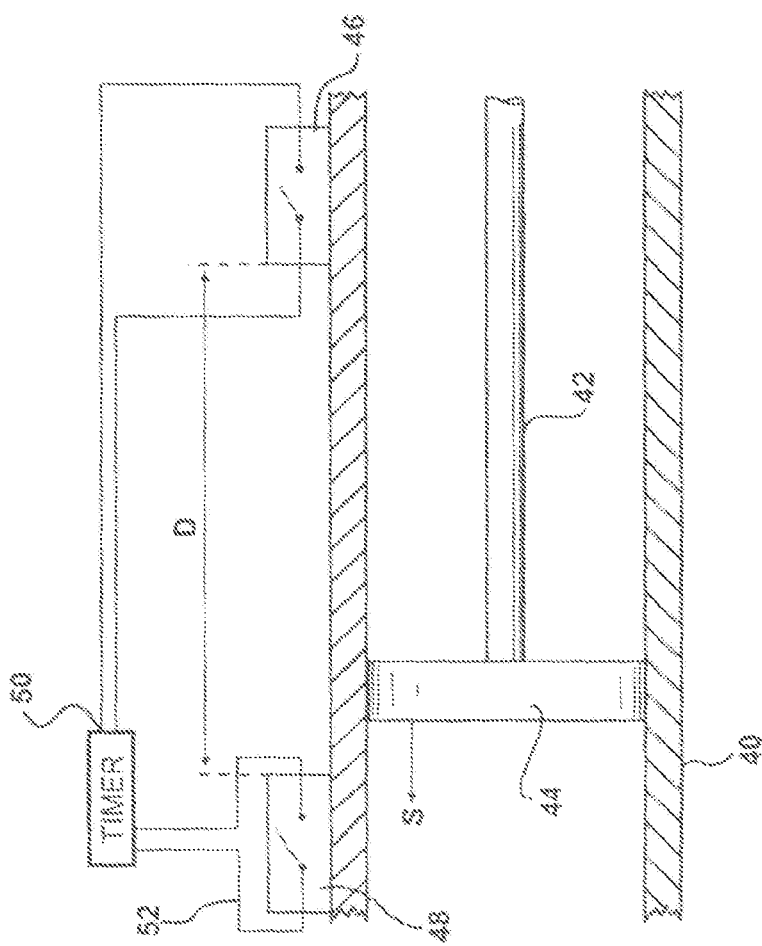

AUTOMATIC SPEED CALCULATION FOR SCRATCH MACHINE

FIELD OF THE INVENTION

The present invention relates to apparatus and methods for material testing, in particular surface testing, such as scratch testing.

BACKGROUND OF THE INVENTION

In order to test the wear resistance of a sample material, such as plastic, resin, or other material, a blade can be dragged across the surface of the sample. The depth and visibility of the scratches can be judged to determine which material is more resistant to scratching.

An example conventional scratch test machine includes five blades, each blade attached to a metal arm, is pulled across the surface of a sample. The design allows different loads to be placed on the arms, in order to determine at which load the sample scratches. In a conventional scratch test machine, hydraulic pressure within a cylinder is adjusted so as to approximately determine the test speed. However, such scratch tests are often irreproducible. Improved surface testing machines are required, in order to obtain more accurate and reproducible surface testing results.

SUMMARY OF THE INVENTION

An apparatus for performing a surface test on a surface of a material comprises a surface contacting element, moving over the surface with a test speed during the test, and an arm assembly, providing an urging force so as to urge the surface contacting element over the surface. The arm assembly includes a magnetic portion that successively actuates a pair of spaced apart magnetic sensors, such as reed switches, located proximate to the arm assembly, and an electronic circuit, receiving electrical signals from the pair of spaced apart reed switches, and determining the time between the successive actuations, and hence the test speed.

For example, the arm assembly can comprise a piston moving within a cylinder during the test, and other components mechanically coupling the piston to the surface contacting element. A magnetic piston can be used as the magnetic portion of the arm assembly. The arm assembly may be driven by hydraulic pressure, or a motor, gravity, manual force, or other force.

An example apparatus for performing a scratch test on a surface of a material comprises a cylinder, a piston moving within the cylinder that is driven by a hydraulic pressure within the cylinder, and a surface contacting element such as a blade moving over the surface at a test speed during the scratch test. The test speed is correlated with the movement of the piston, and may be the same as the piston speed. First and second reed switches are provided proximate to the cylinder, and are spaced apart so that the reed switches are successively actuated by a magnetic portion of the piston as it moves through the cylinder during the scratch test. A timing circuit receives electrical signals from the pair of spaced apart reed switches, and determines a test time between successive actuations of the reed switches during the scratch test, and a test speed from the test time and the spacing of the switches. The test speed can be shown on a display, along with a warning, for example if the test speed is not within an acceptable range, the test speed deviates by an excessive amount from a previous or predetermined test speed, or otherwise is not an acceptable test speed. In one example, the mechanical coupling between the piston and the blade includes a rod, having one end connected to the piston and the other end attached to an arm. The arm is supported by a sliding module that moves along a rail, or is otherwise free to move. The blade is attached to the arm, for example a downwards pointing blade can be provided proximate to an end of the arm distal to the cylinder.

The test speed can be approximately adjustable by control of the urging force, such as hydraulic pressure. However, variable loading of the arm often causes the test speed to deviate from an acceptable value. An acceptable test speed may be determined by test protocol specifications, may be centered on an average test speed, may be specified by the manufacturer, or otherwise defined.

Apparatus according to the present invention provide accurate test speeds despite variations in surface loading and other test conditions. Conventionally, the dependency of results on test speed in a surface test such as a scratch test has not been appreciated. For example, using accurate test speeds, the scratch resistance of a material can be described by a model that includes test speed, allowing improved results compared with using the conventional and inaccurate assumption that test speed remains constant as long as hydraulic pressure is not changed.

A method of performing a scratch test on a surface of a material at an acceptable test speed includes providing a blade in contact with the surface, applying a load on the blade directed against the surface, providing a lateral force (such as derived from hydraulic pressure within a cylinder) to urge the blade across the surface at a test speed approximately correlated with the force, accurately determining the actual test speed (rather than an estimated value obtained from the magnitude of the lateral force) using an electronic timer, and adjusting the lateral force if the test speed is not within an acceptable range of test speeds. The lateral force adjustment can be automatically controlled, using the test speed measurements, to provide an acceptable test speed over a wide range of loads. For example, hydraulic pressure to a cylinder can be adjusted using a fluid valve, such as a pressure regulator, to an extent necessary to provide an acceptable test speed.

BRIEF DESCRIPTION OF THE DRAWINGS

FIG. 2 illustrates a pair of spaced-apart reed switches electrically connected to a timing circuit, the reed switches being energized by a magnetic piston;

FIG. 3 is a generalized schematic of an apparatus according to the present invention.

DETAILED DESCRIPTION OF THE INVENTION

Figure 1:
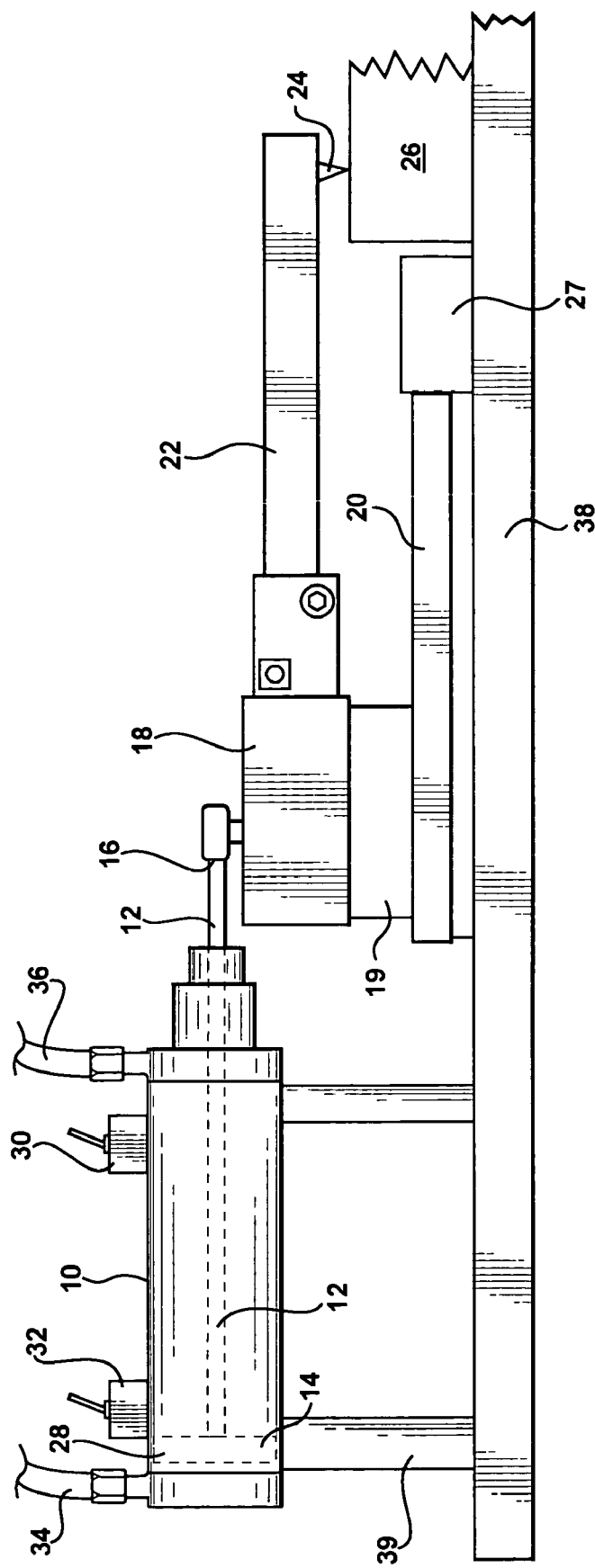
FIG. 1 shows a scratch test machine according to an example of the present invention.

An improved surface testing machine includes a timing mechanism that allows accurate determination of the true test speed during a scratch test or other surface test. The test speed is the speed across the surface of a surface contacting element, such as a blade of a scratch test machine. The test speed can be determined by determining the speed of other components mechanically coupled to the surface testing components, such as the speed of a piston.

For example, uncertainty in scratch test results arises from test speed variations between scratch tests. Conventional machines allow a crude speed control through adjustment of air or other hydraulic fluid pressure to a drive cylinder. However, different loadings of the test arm (or arms) cause test speed variations.

The conventional approach to adjusting test speed is to adjust the urging force, such as hydraulic pressure, urging the blade over the surface. The actual test speed, however, depends on various parameters, in particular the loading of the test arms, and may also depend on surface friction of the sample material, and internal friction within apparatus components. Results have shown that measuring actual test speed, rather than urging force as an indirect proxy for test speed, provided surprisingly better accuracy of results.

Scratch test machines have been available for many decades, yet a convenient and accurate mechanism for test speed determination is not available. This may be due to a failure of others to appreciate the importance of test speed on the results of a scratch test, or the effect of loading on the test speed.

The Five Finger scratch machine is an industry standard machine for measuring the effects of scratches on materials such as various plastic resins. The machine has an arm assembly comprising a cylinder, piston, rod, and five arms, to each of which a blade is attached. Various loads can be placed on the arms, and the machine urges the blades across the surface of the plastic, resin or other material under test. The depth and visibility of any scratches produced are judged, allowing an operator to determine which material is more resistant to scratching. In a conventional apparatus, the speed of the test is controlled by adjusting the hydraulic pressure driving the rod, to obtain a recommended speed. However, changing the applied load (for a given hydraulic pressure) changes the resulting speed of the test, causing the test speed to deviate from the recommended speed. Further, our observations indicate that the speed of the test directly affects the results. For example, a higher speed can cause the fingers to chatter across the specimen instead of smoothly scratching, whereas at the recommended (or other acceptable) test speed this effect does not happen. Hence, the accuracy of the test is compromised by the changing test speed as the load is varied.

Conventional scratch test machines provide no way to accurately measure, or calibrate, the speed of the machine while the test is running. Typically, a given hydraulic pressure is assumed to provide a given test speed. As discussed above, this assumption is not correct.

In examples of the present invention, test timing is measured using spaced apart reed switches proximate to a cylinder installed as part of a scratch test machine. For example, the reed switches may be supported by a cylinder wall. A test time is determined for the blade to pass through a given distance related to the spacing of the reed switches. A look-up table can be used to determine test speed in mm/minute, or other desired units, from measured test times.

The surface contacting element can be a blade (metal, plastic, or other material), edge, abrasive element such as an abrasive surface (such as sandpaper or similar material), mineral, chemical-infused matrix, block, rod, point, cloth, wire, wire mesh or scour pad, electrode (which need not physically contact the surface, but may be in electrical contact with the surface through an electrical discharge or plasma), other elements that can be used to wipe, scratch, abrade, scour, coat, clean, polish, etch, react with (such as oxidize, reduce, corrode, or otherwise chemically modify), or otherwise modify a surface, some combination thereof, or other material or component, contacting the surface of the material.

The arm assembly used to urge the surface contacting element across the surface can include a piston, rod, and cylinder configuration, hydraulic pressure within the cylinder driving the piston, the piston being attached to the rod, the rod being mechanically coupled to the surface contacting element. Examples below are discussed in terms of this configuration, however, the arm assembly may be differently configured without deviating from the scope of the invention, for example including a motor, spring, pendulum, or other drive mechanism.

A scratch test machine according to an example of the present invention includes a cylinder and a rod driven by a fluid within the cylinder. The rod has a first end and a second end. The first end moves within the cylinder, and can be driven by hydraulic pressure, for example of air or oil within the cylinder. The second end is mechanically coupled to one or more test arms, each test arm having a blade.

The first end of the rod can include (or be attached to) a magnetic portion, or may be entirely magnetic. For example, the first end of the rod may be connected to a magnetic piston. Two reed switches are provided, spaced apart, and supported by a wall of the cylinder or otherwise located so as to be successively actuated by the magnetic piston as it moves within the cylinder during a scratch test.

As the first end of the rod moves from a starting position to a finishing position, a first reed switch, and subsequently a second reed switch, are successively actuated by the magnetic piston. The time between the activations of the reed switches is determined using an electronic timing circuit, and the speed of the test is found from the time. The time between reed switch activations T, and a reed switch spacing distance D, are used to determine a test speed S using the equation: $S=D/T$.

If the speed is outside of recommended range, the hydraulic pressure can be adjusted. The test speed may be recorded, and used to correct the results of the scratch test. If the hydraulic pressure is under electronic control, the pressure adjustment can be made automatically based on the speed measurement, so as to maintain an acceptable test speed.

For example, a test speed may have an upper limit arising from skipping of the blade over the surface at unacceptably high test speeds. Test speeds can be monitored as a load on the blade is changed, and the hydraulic pressure can adjusted to maintain an acceptable test speed. For example, an acceptable test speed does not vary by more than approximately +/−2 mm per minute as the load is varied, or does not vary by more than a certain percentage, such 5%, or 2%.

Examples below discuss improved scratch test machines. However, examples of the present invention include other surface testing apparatus, and other material testing apparatus where a test component moves over or through a material, particularly if the test component is driven by a constant force under different load conditions.

FIG. 1 illustrates an apparatus according to the present invention comprising cylinder 10, rod 12, the rod having a first end connected to piston 14, and second end 16 connected to a sliding module 18. The piston 14 is magnetic at least within a portion of the upper part of the piston 28, or the piston 14 can be entirely magnetic. The term magnetic piston includes pistons which include only a magnetic portion, or which are entirely magnetic. The sliding module 18 runs along a rail 20, and the movement of the sliding module is driven by movement of the rod 12. The sliding module has one or more test arms, such as arm 22, extending therefrom. A blade 24, proximate to the distal end of the arm 22, contacts a surface of the sample 26. The rail 20 abuts block 27, which can aid positioning of the sample 26 on the base 38. The cylinder is in part supported on the base by cylinder support 19.

In this example, the arm assembly urging the blade across the surface comprises the piston, rod, sliding module, and arm. There may be a plurality of arms, such as five.

The outer wall of the cylinder 10 supports the first reed switch 30 and second reed switch 32. The cylinder 10 is also provided with two hydraulic fluid connections at opposite ends of the cylinder, namely first fluid connection 34 and second fluid connection 36. The test speed (the speed of the blade across the sample surface, in this example equal to the rod or piston speed) can be roughly controlled by hydraulic pressure adjustment, for example, by adjusting a gas regulator in the case of an air driven rod.

As the piston 14 passes close to a reed switch, the magnetic field provided by the magnetic piston actuates the reed switch, providing electrical communication across the terminals of the reed switch. The time interval between successive switch actuations (as the piston moves from one end of the cylinder to the other end) can be used to determine the speed of the blade over the surface during a scratch test, and hence the test speed of the scratch test. Electrical connections to the reed switches are not shown in this figure. In the figure, the reed switches are represented schematically as mechanical switches. In practice, a reed switch typically comprises a magnetically actuated switch inside a plastic housing, having at least two electrical connections, which are electrically disconnected (open circuit) when the switch is open, and electrically connected (closed circuit) when the switch is closed (or actuated).

For example, in one mode of operation, the piston moves from right to left during a scratch test. The blade is drawn across the surface of the sample 24 in a direction towards the cylinder 10. The first reed switch is actuated by the magnetic portion near the start of the test, turning on a timing circuit. The second reed switch, proximate to the other end of the cylinder, is actuated near the end of the test, turning off the timing circuit. The timing circuit is not shown in this figure, and will be discussed in more detail below. As the reed switch spacing is known, the time between successive reed switch actuations can be used to determine a test speed.

FIG. 2 shows more detail of a possible reed switch configuration. FIG. 2 shows cylinder 40, rod 42 connected to a magnetic piston 44, and first and second reed switches 46 and 48. An electronic timer 50 is in electrical communication with the spaced apart pair of reed switches, and determines a time interval between successive activations of the reed switches. The timer may determine a time interval between a first time at which the first reed switch is actuated (turns on, or connection closed) and a second time at which the second reed switch is actuated (turns on).

Other configurations can be used, with appropriate corrections, if necessary. For example, a time interval may be determined between times at which both switches turn off, or between mid-times of turn on periods, or between a first switch turning off and a second switch turning on, or some other combination, as long as the reed switch spacing used is appropriately chosen.

The switches turn on, or are actuated, when the magnetic piston is proximate to the switch. If the switches are substantially identical, the sensitivities will be approximately the same, hence the distance between actuation points will be approximately the same as the spacing of the mid-point of the switches. In this figure, D represents a reed switch separation, which may be slightly less than the reed switch spacing used to calculate test speed. The reed switch spacing used to determine test speed will be approximately the distance D, but a correction can be made for the finite widths of the reed switches. Corrections can also be made for sensitivity variations of the reed switches. The reed switch spacing used is the distance corresponding to the determined time interval.

The reed switches (or other magnetic sensors) can be placed proximate to the start and end of a test run, so that a first switch turns on at the beginning of the test and the second switch turns off just before the end of the test. The test speed measurement determines an average speed during the test, hence if the reed switches are separated by substantially the length of the test, an average speed for the whole surface test, such as a scratch test, is determined.

The reed switches may be separated by a distance corresponding to a portion of the test, and an average speed can be determined for that portion of the test. A corresponding portion of the sample surface, corresponding to the determined average speed, can be marked on the sample, or indicated using guide marks on the apparatus.

In other examples, multiple reed switches can be provided, enabling speed values to be determined over various portions of a test if desired.

FIG. 3 shows a general schematic of an apparatus according to an example of the present invention, having first sensor 60, second sensor 62, timing circuit 64, display 66, and reset button 68, the first and second sensors being spaced apart by a sensor spacing distance D. The sensors may respond to, for example, a magnet attached to any moving part of a scratch test machine during a scratch test, such as a magnetic portion of the arm assembly.

Using a magnetic piston, or other magnetic component, a sensor may include a reed switch, coil, other inductive device, or other sensor component sensitive to a magnetic field, such as a sensor using the Hall effect, magnetoresistance (including giant magnetoresistance) effect, magnetooptical effect, or other magnetic field induced response. In other examples, metal in the piston can be detected using, for example, a metal sensor (metal detector), for example including an inductor. The piston position may also be continuously determined from the magnetic field sensed by one or more magnetic field sensors along the cylinder, and speed determined from the time-dependent position data. For example, a magnetic sensor may be actuated by a magnetic portion of the arm assembly when the sensor provides a signal correlated with the close proximity, or passing by, of the magnetic portion. In this context, actuation of a sensor refers to generation of a sensor signal correlated with close proximity of the sensed portion of the arm assembly or other apparatus component moving during the scratch test in a manner correlated with the test speed.

In other examples, optical sensors can be used. For example, if at least part of the cylinder is transparent, optical signals may be determined as the rod end passes the sensor. In this case, the sensor may be a photodiode, phototransistor, or may comprise an optocoupler. The rod end may be light emitting, or background illumination may be provided. Video imaging may also be used.

Figure 4:
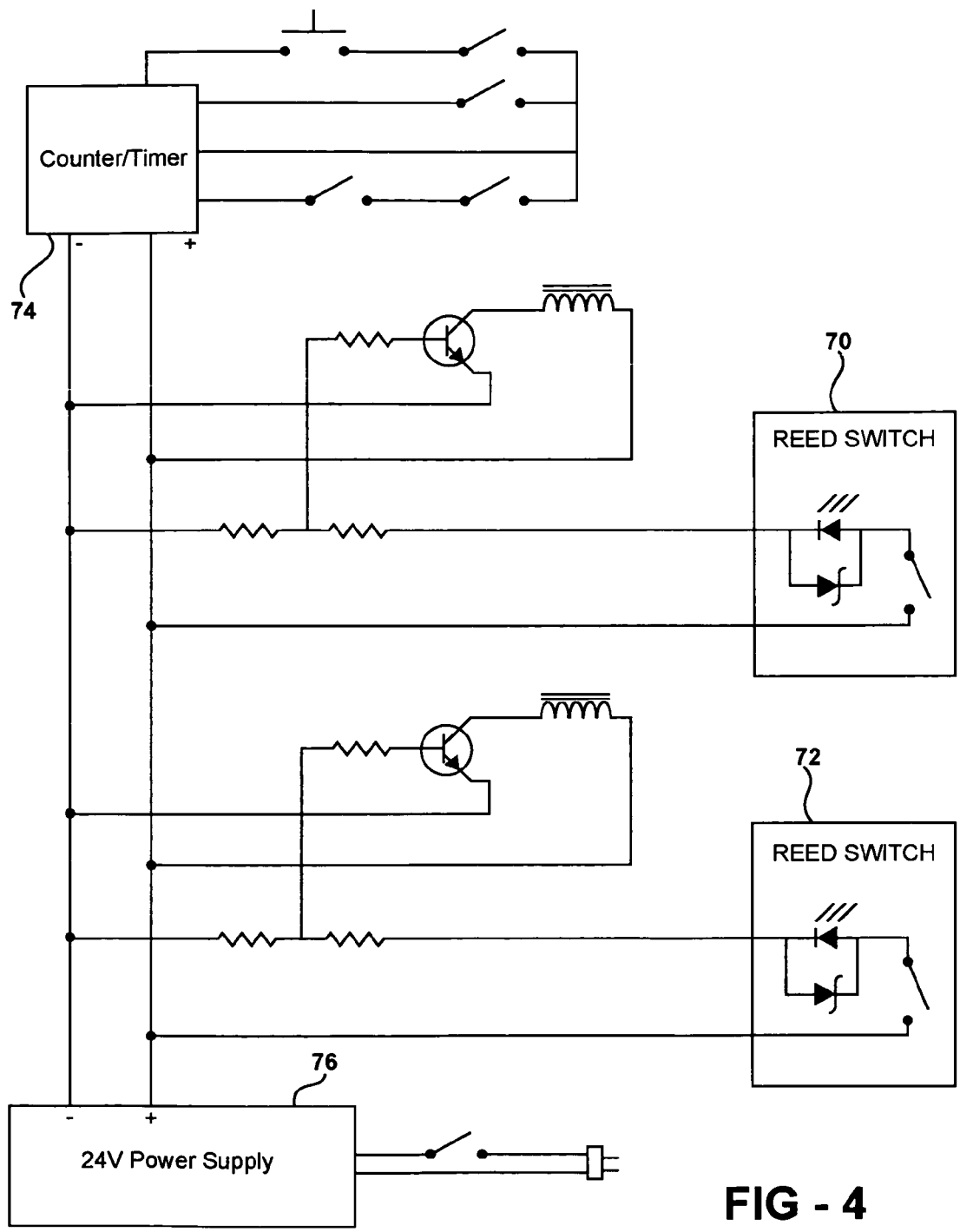
FIG. 4 is a schematic of a timing circuit which may be used in examples of the present invention.

FIG. 4 is a schematic of a timing circuit which may be used in examples of the present invention, for example for the apparatus discussed in relation to FIG. 1. The first and second reed switches 70 and 72, respectively, are placed on or proximate to the cylinder so as to be actuated by a magnetic portion of the rod. The magnetic portion can be a part of (or all of) the piston, or other part of an arm assembly.

The circuit includes an Omron™ H8CA counter timer integrated circuit, 74. Other components, including power supply 76, are provided in a conventional timing circuit, the operation of which will be familiar to those skilled in the electronics arts and will not be further discussed. A time interval, corresponding to a count, is determined between successive switch operations. A reset button allows the time to be zeroed at the end of each test.

The output of a timing circuit can be provided to a computer, displayed on an alphanumeric display, or provided to another analytical instrument or instrument controller. The display timed can be scaled to convenient units, such as millimeters per second.

The timer output can also be used to automatically adjust hydraulic fluid pressure (such as air or oil pressure) to obtain a desired test speed, or to allow calibration of a hydraulic pressure regulator. For example, a calibration function can be determined in terms of hydraulic pressure (such as air pressure), load on the sample, and test speed. Other parameters, such as sample surface properties (such as topography or friction), humidity, temperature, and/or other parameters which may influence the test results.

OTHER EXAMPLES

Other surface testing equipment, according to the present invention, may include surface abrasion apparatus, in which an abrasive pad is passed across a surface of the sample. The apparatus may have a structure otherwise analogous to those discussed above. Other surface tests provided by apparatus according to the present invention can include surface profiling, surface scouring or abrasion (forms of scratch test), cleaning (for example, in which chemical is applied to a surface through a pad), polishing, and the like.

The arm may move backwards and forwards across the material, or may move only in one direction. In examples discussed in detail above, a typical scratch test is perfumed by moving the blade towards the cylinder. Gearing may be provided between the rod and the arm, in which case the determined test speed is calculated using a known gearing parameter.

In other examples, the cylinder may be omitted and arm assembly (which may include one or more of an arm, rod, or other mechanical component) may be urged over the surface of the sample material by a motor, spring, elastic, gravity, manual, or other force. For example, the arm assembly may include the drive shaft of a motor, or component attached thereto.

The examples above disclose reed switches supported by the cylinder. The reed switches may be disposed at any convenient location proximate to the cylinder, for example underneath, or to the sides or above the cylinder. In other examples, the test arm or blades of a scratch test device may include magnetic portions, the motion of which is sensed using one or more reed switches located in suitable locations proximate to points on the motion path of the magnetic portion. The reed switches may be located in any suitable location, for example, proximate to the test arm if the arm has a magnetic portion.

The sensors, such as reed switches, may illuminate when actuated. The illumination may provide an optical signal that is detected by a remote timing circuit. In this example, an optical connection, such as a fiber, can be provided between the reed switches and the timing circuit. This may be valuable where the cylinder is remote from the timing circuit.

Hence, an improved scratch test machine is provided. Qualitative evaluation of the scratch resistance of resins, plastics, and other materials is dependent on the test speed. Current industry standard machines, such as the Ford Five Finger scratch machine, have no method to directly measure the test speed. A stopwatch can be used, but this provides inaccurate results. An improved apparatus, according to the present invention, provides accurate test speed measurements, allowing reproducible results of improved accuracy. Example apparatus according to the present invention measure the time of a scratch test over the length of at least a portion of a scratch test, allowing an average test speed to be calculated from the determined time and a known spacing of the sensors used, such as reed switches. The apparatus can be separately calibrated for any desired load combination used during a test, which can assure constant speed during all test conditions. A load sensor can be used to send an electrical signal to a hydraulic pressure control, to adjust hydraulic pressure for test speed consistency. Hydraulic pressure can also be adjusted manually for each load, using a calibration function in terms of load, hydraulic pressure, and test speed.

The apparatus may also include a display, providing a visual representation of test speed, such as an analog gage, digital readout, or the like. A visual or audible warning may also be provided if test speed is not within an acceptable range of test speeds, for example using a warning lamp or message.

An improved apparatus, according to the present invention, comprises a pair of spaced-apart reed switches and an electrical timing circuit. The test speed is measured from a time interval measured between activation of a first reed switch and a second reed switch. This time interval is used with a predetermined distance to calculate the test speed, thereby allowing calibration of the apparatus for each load.

Commercially available cylinder rods having a magnetic end are available and may be used in examples of the present invention. Similarly, reed switches are readily available from electrical component suppliers.

Hence, an apparatus for performing a scratch test on a surface of a material according to an example of the present invention comprises a cylinder, a piston moving within the cylinder that is driven by hydraulic pressure within the cylinder, and a blade moving over the surface at a test speed during the scratch test. The blade movement is mechanically coupled to the movement of the piston, so that the test speed is approximately controlled by the hydraulic pressure. A pair of spaced apart reed switches are provided proximate to the cylinder, the reed switches being successively actuated by, for example, a magnetic portion of the piston as it moves through the cylinder during the scratch test. A timing circuit determines a test time between successive actuations of the reed switches during the scratch test, and a test speed from the test time and the spacing of the switches. Test speeds can be monitored as a load on the blade is changed, and the hydraulic pressure adjusted to maintain an acceptable test speed, for example one that does not vary so much as to compromise the accuracy of the scratch test. A hydraulic fluid may be air, oil, or a combination, such as an air over hydraulic movement. A cylinder may be controlled only by air pressure, in which case speed variations often occur over the sample. However, the addition of oil tends to dampen this variation. The features of conventional scratch test apparatus are known to those skilled in the art. In an improved scratch test, the test speed is kept substantially uniform (within approximately +/−2 mm per minute) independent of the load applied and material tested. Such an improved scratch test has not been possible with conventional apparatus.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims. Patents, patent applications, or publications mentioned in this specification are incorporated herein by reference to the same extent as if each individual document was specifically and individually indicated to be incorporated by reference.

Having described our invention, we claim:

1. An apparatus for performing a surface test on a surface of a material, the apparatus comprising:
   a surface contacting element, moving over the surface with a test speed during the surface test;
   an arm assembly, urging the surface contacting element across the surface during the surface test, the arm assembly having a magnetic portion;
   a pair of spaced apart magnetic sensors located proximate to the arm assembly, the magnetic sensors being successively actuated by the magnetic portion during the surface test; and
   an electronic circuit, receiving electrical signals from the pair of spaced apart magnetic sensors, the electronic circuit determining the test speed using the electrical signals.

2. The apparatus of claim 1, wherein the arm assembly comprises:
   a piston moving under hydraulic pressure during the surface test; and
   an arm, mechanically coupled to the piston, the surface contacting element being attached to the arm.

3. The apparatus of claim 2, wherein the piston is a magnetic piston, the magnetic piston providing the magnetic portion of arm assembly.

4. The apparatus of claim 1, wherein the magnetic sensors are reed switches.

5. The apparatus of claim 1, wherein the surface contacting element is a blade.

6. The apparatus of claim 1, wherein the electronic circuit includes a digital timing circuit operable to determine a test time between successive actuations of the magnetic sensors during the surface test.

7. The apparatus of claim 1, wherein the electronic circuit accesses a look-up table to determine the test speed from the test time.

8. The apparatus of claim 1, further comprising a display, the display providing a visual indication of the test speed.

9. The apparatus of claim 1, wherein the arm assembly provides a support surface for a load.

10. An apparatus for performing a scratch test on a surface of a material, the apparatus comprising:
    a cylinder;
    a piston moving within the cylinder during the scratch test, the piston being driven by hydraulic pressure within the cylinder, the piston having a magnetic portion;
    a blade, moving over the surface during the scratch test, the blade moving with a test speed;
    a mechanical coupling between the piston and the blade, so that the test speed is correlated with a piston speed;
    a pair of spaced apart reed switches located proximate to the cylinder, the reed switches being successively actuated by the magnetic portion as the piston moves through the cylinder during the scratch test; and
    an electronic circuit, receiving electrical signals from the pair of spaced apart reed switches, the electronic circuit determining the test speed.

11. The apparatus of claim 10, wherein the mechanical coupling between the piston and the blade comprises:
    a rod, having a first end and a second end, the first end of the rod being connected to the piston;
    a sliding module, connected to the second end of the rod; and
    an arm, supported by the sliding module, the blade being attached to the arm.

12. The apparatus of claim 11, comprising a plurality of arms, each arm being attached to a different one of a plurality of blades.

13. The apparatus of claim 11, wherein the arm is supported by a sliding module.

14. The apparatus of claim 10, the cylinder having a cylinder wall, the pair of spaced apart reed switches being supported by the cylinder wall.

* * * * *